(12) United States Patent
Fratter

(10) Patent No.: US 9,289,738 B2
(45) Date of Patent: Mar. 22, 2016

(54) NANOEMULSION, METHOD FOR ITS PREPARATION AND USE

(75) Inventor: Andrea Fratter, Scorze' (IT)

(73) Assignee: EMULTEC S.r.l., Istrana, Treviso (IT)

( * ) Notice: Subject to any disclaimer, the term of this patent is extended or adjusted under 35 U.S.C. 154(b) by 332 days.

(21) Appl. No.: 13/515,846

(22) PCT Filed: Dec. 15, 2009

(86) PCT No.: PCT/IB2009/055754
§ 371 (c)(1), (2), (4) Date: Jun. 14, 2012

(87) PCT Pub. No.: WO2011/073726
PCT Pub. Date: Jun. 23, 2011

(65) Prior Publication Data
US 2012/0251596 A1    Oct. 4, 2012

(51) Int. Cl.

| | |
|---|---|
| *B01F 17/00* | (2006.01) |
| *A61K 47/12* | (2006.01) |
| *A61K 47/10* | (2006.01) |
| *A61K 8/67* | (2006.01) |
| *A23L 3/3517* | (2006.01) |
| *A61K 8/19* | (2006.01) |
| *A23D 7/01* | (2006.01) |
| *A61K 8/06* | (2006.01) |
| *A61K 8/86* | (2006.01) |
| *A61K 31/4045* | (2006.01) |
| *A61Q 19/00* | (2006.01) |
| *A61K 9/107* | (2006.01) |
| *A23D 7/005* | (2006.01) |
| *A61K 47/26* | (2006.01) |

(52) U.S. Cl.
CPC .......... *B01F 17/0092* (2013.01); *A23D 7/0053* (2013.01); *A23D 7/011* (2013.01); *A23L 3/3517* (2013.01); *A61K 8/06* (2013.01); *A61K 8/19* (2013.01); *A61K 8/676* (2013.01); *A61K 8/86* (2013.01); *A61K 9/1075* (2013.01); *A61K 31/4045* (2013.01); *A61K 47/10* (2013.01); *A61K 47/12* (2013.01); *A61K 47/26* (2013.01); *A61Q 19/00* (2013.01); *A61K 2800/10* (2013.01); *A61K 2800/21* (2013.01)

(58) Field of Classification Search
None
See application file for complete search history.

(56) References Cited

U.S. PATENT DOCUMENTS

2008/0207777 A1    8/2008    Auweter et al.

FOREIGN PATENT DOCUMENTS

| WO | 2007003565 A1 | 1/2007 |
|---|---|---|
| WO | 2007060177 A1 | 5/2007 |

OTHER PUBLICATIONS

Tan et al., "Melatonin: a potent, endogenous hydroxyl radical scavenger" Endocrine J 1: 57-60 (1993).*
Chobert et al., "Solubility and Emulsifying properties of kappa casein and its caseinomacropeptide", J Food Biochem 13: 457-473 (1989).*
Veerawat Teeranachaideekul, Varaporn B. Junyaprasert, Eliana B. Souto, Rainer H. Muller, Development of ascorbyl palmitate nanocrystals applying the nanosuspension technology, International Journal of Pharmaceutics, 354 (2008) 227-234.
Helmut Sapper, David G. Cameron, Henry H. Mantsch, The thermotropic phase behaviour of ascorbyl palmitate: an infrared spectroscopic study, Can. J. Chem. 59, 2543 (1981).

* cited by examiner

*Primary Examiner* — Robert A Wax
*Assistant Examiner* — Thor Nielsen
(74) *Attorney, Agent, or Firm* — Robert E. Alderson, Jr.

(57) ABSTRACT

Nanoemulsions comprising an aqueous phase and a lipid phase, having a micelle size in the range from about 20 to about 900 nm and comprising melatonin as an active agent, are provided. The aqueous phase of such a nanoemulsion comprises a base, the lipid phase comprises one or more polyoxyethylene sorbitan esters, and the aqueous phase or the lipid phase, or both, further comprise ascorbyl palmitate. In addition, pharmaceuticals, cosmetics or foodstuffs comprising the nanoemulsions described herein and methods for making nanoemulsions described herein are also provided.

14 Claims, No Drawings

NANOEMULSION, METHOD FOR ITS PREPARATION AND USE

CROSS-REFERENCE TO RELATED APPLICATIONS

This application is a National Phase Application of PCT International Application No. PCT/IB2009/055754, International Filing Date, 15 Dec. 2009, which is hereby incorporated by reference in its entirety.

FIELD OF THE INVENTION

The object of the present invention is a stable nanoemulsion with a reduced micelle size, a composition comprising such a nanoemulsion and a method for the preparation thereof. The nanoemulsion described herein is particularly, but not exclusively, used in the pharmaceutical, cosmetic, and foodstuff fields.

BACKGROUND OF THE INVENTION

The nanoemulsions are heterogeneous polyphasic systems wherein at least one phase is dispersed in the form of nanoparticles (nanodroplets) in the outer continuous aqueous phase. As for the classical emulsions, the presence of a surface-active system, which is capable of decreasing the interface tension that is very high in these systems, is essential due to the high number of dispersed-phase particles. The surfactant creates an amphiphilic crown on the surface of the dispersed-phase droplets, thereby reducing the interface tension.

Due to the reduced micelle diameter that minimises the possibility of interaction with light and ultraviolet quanta (hv), the nanoemulsions appear transparent and translucent and take on a characteristic "bluish Tyndall" colouring, characterised by a tendency to opalescent blue. The Tyndall effect is a light dispersion phenomenon due to the presence of dispersed particles with a size comparable to that of the incident light wavelength. Thus, in such dispersions, the incident light is reflected in every direction.

In order to be able to obtain nanoemulsions, it is necessary to exert strong stresses in terms of kinetic and thermal energy during emulsification, as well as the use of emulsifiers designed to decrease in a very effective way the micelle interface tension that opposes the diameter reduction thereof, according to LaPlace and Stokes-Einstein rules.

According to LaPlace rule, the pressure gradient between the outer and inner phases ($\Delta P$) corresponds to twice the ratio of the liquid/liquid interface tension between the inner phase micelle (T) and the micelle radius (r), that is: $\Delta P = 2T/r$. From this equation, the tight connection between the inner phase micelle radius and the inner and outer differential pressure is inferred, which is expressed as the required force to be applied to the biphasic system in order to minimise the radius and interface tension of the micelle itself. In fact, the pressure, being inversely proportional to the radius, increases with the decrease of the latter and thus the $\Delta P$ value corresponds to the pressure to be overcome in order to decrease the particle size. For this reason, not only high concentrations of surfactants that decrease the interface tension must be used, but also considerable kinetic and thermal forces must by applied in order to reach a stability.

The nanoemulsion stability also depends on Stokes-Einstein rule, according to which $v = 2r^2 (d_1 - d_2) g / 9\eta$, wherein v represents the sedimentation rate, r the radius of the dispersed particles, $d_1$ the density of the dispersed particles, $d_2$ the density of the continuous phase, g the gravitational constant and $\eta$ corresponds to the viscosity of the continuous phase. This rule regulates the sedimentation rate for a supposedly spherical particle, pointing out that the sedimentation rate is proportional to the size of the dispersed particle and thus confirming the importance of the surface-active system. In the case of nanoemulsions, wherein the inner particles exhibit a diameter smaller than 0.5 µm, such a rule becomes less important, in that the particles are not subjected to the acceleration of gravity, but are subjected to Brownian motions. Therefore, in order for the particles to sediment, a force higher than the gravitational one is necessary.

The nanoemulsions, as they are not equilibrium systems, can not form spontaneously because the system attains a thermodynamic stability only if the interface tension reaches values that are sufficiently low such that the positive interface energy can be compensated for. The known methods for the formation of nanoemulsions are of a mechanical type and comprise the use of high-energy instruments such as, for example, high-energy mixers, high-pressure homogenizers, or ultrasounds. Using such instruments allows to deform the forces that keep the particles joined, such that they can break into smaller units. However, in order to obtain such a result, it is necessary to overcome the pressure gradient described by LaPlace rule, for instance by adding surfactants. Nevertheless, these preparation methods are complex and costly, therefore simpler solutions based on exploitation of the chemophysical properties of the system have been sought.

One first method of this kind is based on the so-called "Taylor instability" and consists in modifying the formulation such that the micro-emulsion particles merge and break into smaller particles at the time when the interface tension is increased. However, due to the high degree of coalescence that develops during the processing, the method turns out to be rather complex. In fact, the droplets tend to combine rapidly, thereby forming bigger drops. It is however possible to obviate this phenomenon by exploiting the Phase Inversion Temperature (PIT), thanks to which a liquid crystal layer can form, which is able to encapsulate the droplets.

A second type of method exploits phase inversion. One first possibility is based on the so-called "catastrophic phase inversion", wherein an emulsion containing water-in-oil drops suddenly turns into an oil-in-water dispersion or vice versa. Recent researches have shown that in some cases such an inversion can occur by passing through an intermediate structure designated as "multiple emulsion", wherein the continuous phase is able to deform and create smaller drops embedded in the bigger ones. When this multiple emulsion finally breaks it can release small droplets. The second possibility is instead based on the traditional phase inversion, wherein the spontaneous reorganisation of the surfactant micelles is exploited.

The size of the droplets within the nanoemulsions is so small that gravity has no effect on them: they will not sediment until the drop size increases by coalescence through Brownian motions or other processes called "Ostwald ripening", which are controlled by the pressure gradient of Laplace rule existing among droplets of different sizes. Such sedimentation mechanisms can be, as previously already stated, inhibited by using a set of appropriate solvents and preparing an emulsion the most monodisperse as possible.

Therefore, there exists a need for a stable nanoemulsion having a reduced micelle size, which is able to carry a wide range of pharmaceutical, cosmetic or foodstuff active principles, and the making of which does not require the use of complex or costly methods or devices.

SUMMARY OF THE INVENTION

The main task of the present invention is to provide a stable nanoemulsion having a reduced micelle diameter.

In the scope of such a task, one object of the invention is to provide a nanoemulsion that can be manufactured with a reduced energy waste in terms of agitation and heating energy.

Another object of the invention is to provide a nanoemulsion with the ability to carry active principle molecules of interest in the pharmaceutical, cosmetic or foodstuff field.

Still another object of the present invention is to provide a nanoemulsion that is also able to carry thermolabile or oxidation- and destabilization-sensitive active principle molecules.

Moreover, the present invention intends to provide a nanoemulsion, the transparency and viscosity of which can be easily modulated so as to make the nanoemulsion itself suitable for a number of types of application.

Furthermore, the present invention has the object of providing a method for the manufacture of a nanoemulsion as described herein.

Not least of all, the invention has the object of providing a nanoemulsion and a method for the preparation thereof, which are highly reliable, relatively easy to perform, and cost-effective.

DETAILED DESCRIPTION

Such a task, as well as these and other objects that will appear better below, are attained through a nanoemulsion comprising an aqueous phase and a lipid phase, which has a micelle size from 20 to 900 nm, the said aqueous phase comprising an alkalising agent, the said lipid phase comprising one or more polyoxyethylene sorbitan esters, and the said aqueous phase or lipid phase or both further comprising ascorbyl palmitate.

The task and the objects of the invention are also obtained by a method for the preparation of a nanoemulsion having a micelle size from 20 to 900 nm, comprising the steps of:
  (a) preparing an aqueous phase comprising an alkalising agent and optionally one or more polyols, and a lipid phase comprising a lipid and one or more polyoxyethylene sorbitan esters and optionally one or more essential oils, wherein the aqueous phase or the lipid phase or both further comprise ascorbyl palmitate;
  (b) heating the aqueous phase and the lipid phase at a temperature from 30 to 80° C.;
  (c) pouring out the aqueous phase into the lipid phase under mechanical stirring, so as to obtain a nanoemulsion;
  (d) adjusting the nanoemulsion to room temperature.

Preferably, step (d) is performed by abruptly cooling the system under forced circulation of cold water, so as to reach a temperature <30° C. as fast as possible, preferably within 60 minutes from the emulsification.

Moreover, the task and the appointed objects are also attained by a pharmaceutical, cosmetic or foodstuff composition comprising the nanoemulsion herein described.

Finally, the task and the appointed objects are also attained by the use of the nanoemulsion described herein for the manufacture of a pharmaceutical, cosmetic or foodstuff composition.

Other objects, features, and advantages of the invention will be further set out in the following detailed description. Some of the features of the invention will be further set out in reference to the single aspects of the invention itself. In this connection, it is understood that such features are to be intended as valid, whenever applicable, with reference to the nanoemulsion, the composition, and the method, even if not explicitly repeated.

In the following description, the amount of each substance composing the nanoemulsion is indicated in terms of weight percentage of the substance or component based on the weight of the nanoemulsion (% w/w), unless differently stated.

The present invention relates to a nanoemulsion having a reduced micelle diameter and a method for the preparation thereof. According to the invention, the association of two different emulsifying agents allows to provide a nanoemulsion having a micelle diameter from 20 to 900 nm, preferably from 20 to 200 nm, even more preferably from 20 to 100 nm, with a reduced energy consumption in terms of agitation and heating energy. The nanoemulsion is achievable by mixing an aqueous phase comprising ascorbyl palmitate and a lipid phase comprising one or more polyoxyethylene sorbitan esters. Preferably, ascorbyl palmitate is comprised in both the aqueous phase and the lipid phase.

Ascorbyl palmitate (ASP) is the ester of L-ascorbic acid and palmitic acid ($C_{16}H_{3}O_{2}$). This compound is used in the cosmetic and foodstuff fields as an antioxidant and stabilising agent in emulsified systems, particularly as an anti-rancid antioxidant for fats (E304). In cosmetics, ASP is also used as a dermal-absorbable form of L-ascorbic acid.

In the present invention, ASP is used as a co-emulsifier in combination with one or more polyoxyethylene sorbitan esters, in a concentration substantially higher than that needed for its anti-oxidising action in the same system.

The use of ASP as a co-emulsifier has the advantage of allowing for the achievement of the nanoemulsion by applying a decreased thermal and mechanical energy, in particular without requiring the use of high-pressure turbo-emulsifiers and/or homogenisers, or the application of ultrasounds, as the so prepared chemo-physical system can be substantially considered as auto-emulsifying.

ASP behaves as a surfactant molecule by virtue of its amphiphilic structure deriving from the concomitant presence of a hydrophilic portion (L-ascorbic acid) and a lipophilic portion (palmitic acid) in the molecule. As other surfactants, ASP in an aqueous dispersion gives rise to micelle clusters having different geometries as a function of concentration. Such micelle clusters are able to incorporate molecules insoluble or sparingly soluble in water (The thermotropic phase behavior of ascorbyl palmitate: an infrared spectroscopic study Helmut Sapper, David G. Cameron, and Henry H. Mantsch Can. J. Chem./Rev. can. chim. 59(16): 2543-2549).

In an aqueous dispersion, ASP is sparingly soluble and, at concentrations of 2-3%, it is possible to resort to high temperatures for dissolution. Upon standing, depending on concentration, the dispersion gives rise to a yellow dense gel or "coagel", a solid-consistency white layer that may be reconverted into a liquid micelle dispersion (clear yellow) by mild heating. Since the ASP molecule exhibits two acidic hydroxyls (enediol), it is possible, in an aqueous dispersion, to give rise to clear solutions even without heating by formation of an ASP salt by adding an alkaline substance (base).

Therefore, the aqueous phase of the nanoemulsion described herein also comprises a base, preferably in a quantity sufficient to induce ASP ionization and aid its dissolution in water and subsequent emulsifying action when in contact with the lipid phase. The base may be an organic substance, such as for example L-arginine, L-lisine, a peptide or aminomethylpropanol (AMP), or an inorganic substance, such as an alkaline or alkaline earth metal hydrate, for instance NaOH, KOH, $Ca(OH)_2$, or $Ba(OH)_2$. Preferably, the metal hydrates are used in a diluted form in aqueous solutions, for example at 30% w/w.

In fact, it has been observed that it is possible to obtain aqueous dispersions of ASP salts with a base even at concentrations ranging from 2 to 12% w/w. Such a feature emphasizes the propensity of ASP to form water soluble micelles and increases its carrying effectiveness. With the gel it is possible to moisten insoluble powders (amino acids, functional molecules as terpenes or flavonoids) or insoluble plant extracts, giving rise to a granulate that can be dispersed in water resulting in translucent, homogeneous dispersions with a low amount of sediment that, by the way, may be dispersed simply by stirring.

In one embodiment of the present invention, the nanoemulsion may comprise ascorbyl palmitate in a quantity from 0.3 to 2% w/w, preferably from 0.5 to 1% w/w, even more preferably 0.75% w/w.

Polyoxyethylene sorbitan esters (ESP) are non-ionic surfactant molecules characterised by a high hydrophilic-lipophilic balance (HLB), also referred to as polysorbates or TWEEN. These molecules are used in the cosmetic, pharmaceutical and foodstuff fields in emulsifying systems of the oil-in-water type because of their low toxicity profile, high application versatility, and neutrality with regard to the organoleptic and chemo-physical properties thereof.

In one embodiment of the present invention, the nanoemulsion may comprise one or more polyoxyethylene sorbitan esters in a quantity from 0.2 to 10% w/w, preferably from 2% to 10% w/w.

Preferably, the one or more polyoxyethylene sorbitan esters may be selected from the group consisting of polyoxyethylene-(20)-sorbitan monolaurate (polysorbate 20), polyoxyethylene-(20)-sorbitan monopalmitate (polysorbate 40), polyoxyethylene-(20)-sorbitan monostearate (polysorbate 60), polyoxyethylene-(20)-sorbitan tristearate (polysorbate 65), and polyoxyethylene-(20)-sorbitan monooleate (polysorbate 80). Even more preferably, the polyoxyethylene sorbitan ester is polysorbate 60.

In another embodiment, the emulsifying composition may further comprise glycomacropeptide (GMP).

GMP is a glycopeptide, a purified casein fraction, obtained by treating cow's milk with chymosin during the manufacture of cheese. The glycosilation portion is represented by sialic acid and it accounts for approximately 8% in weight of GMP. MP, as the proteins in general, is capable of performing an emulsifying action ascribed to the concomitant presence in the molecule of a lipophilic backbone of carbon atoms and functional hydrophilic groups along such a backbone, among which carboxyl groups and amino groups, which can form salts.

Therefore, GMP may be used as an ASP and ESP co-adjuvant in the nanoemulsion described herein. Particularly, according to the present invention, GMP may be comprised in the nanoemulsion in a quantity from 0.2 to 5% w/w.

In another embodiment, the aqueous phase of the nanoemulsion may further comprise a preserving agent. The preserving agent may be, for example, selected from the group consisting of potassium sorbate, sodium benzoate, parabens, and mixtures thereof.

In a further embodiment, the lipid phase of the nanoemulsion may comprise one or more triglyceride lipids with different carbon chain lengths, preferably two lipids. For instance, such lipids may be the products known by the trademarks Migliol 810, Migliol 812, Delios C, Delios V or Cetiol LC, all from Cognis.

Preferably, the one or more lipids may be selected from the group consisting of coconut oil, wheat germ oil, sunflower oil, olive oil, and a medium-chain triglyceride. More preferably, the lipid is a medium-chain triglyceride (MCT). Particularly, the medium-chain triglyceride may be a C8-C10 triglyceride (caprylic-capric triglyceride), for example derived from coconut oil.

Also, the lipid phase of the emulsion may be represented by, or comprise, oils extracted from fish or algae rich in omega-3 fatty acids, such as EPA and DHA in various ratios.

Preferably, the lipid phase may be made up of oils titrated in EPA and DHA contained in various ratios.

Preferably, the one or more above-mentioned lipids may be used in a quantity ranging from 0.1 to 10% w/w of the nanoemulsion, more preferably from 0.5 to 5.0% w/w.

One or more further plant essential oils may be introduced into the lipid phase in concentrations ranging from 0.05 to 5% w/w, based on the nanoemulsion.

Preferably, the one or more lipids may be used in a quantity from 0.1 to 10% w/w of the nanoemulsion, more preferably from 0.5 to 5.0% w/w.

In another embodiment, the lipid phase of the nanoemulsion may further comprise one or more polyols in a quantity from 0.1 to 40% w/w, more preferably from 0.5 to 20% w/w, based on the nanoemulsion.

The one or more polyols may be, for example, selected from the group consisting of glycerine, propylene glycol, sorbitol, mannitol, fructose, sucrose, glucose, trehalose, and honey, and mixtures thereof.

The nanoemulsion according to the invention may be used in the manufacture of compositions, for instance in the foodstuff, pharmaceutical or cosmetic fields. Therefore, in a further embodiment, the nanoemulsion may also comprise one or more active principles in a quantity from 0.1 to 10% w/w, preferably from 0.1 to 5%. The one or more active principles may be of a hydrophilic, lipophilic or amphiphilic nature, and depending on such a nature, may be comprised in the lipid or aqueous phase of the nanoemulsion.

For example, the one or more active principles may be selected from the group consisting of flavonoids, flavones, flavanones, isoflavones, essential oils, plant terpenes and saponins, liposoluble vitamins, vitamin cofactors, enzyme cofactors, amino acids, oligopeptides, peptides, unsaturated fatty acids, and pharmaceutical active principles. The vitamin and enzyme cofactors may be, for example, lipoic acid, coenzyme Q10 and its derivatives.

In a preferred embodiment, the nanoemulsion comprises ESP and ASP as an emulsifier and co-emulsifier, respectively (preferably as the sole emulsifying agents), in combination with essential oils and/or terpenes.

One may modulate the emulsion transparency by changing the pH of the system, so as to modify the diameters of the nanoemulsion micelles.

The nanoemulsion may be, for example, characterised by a basic or slightly acidic pH, between 5 and 7, at which a high transparency is obtained, due to an increased surfactant action of ASP that, in such a range, results completely ionized within the hydroxylic portion. The increase in transparency is accompanied by a decrease in the micelle diameters and viscosity. Particularly, the decreased viscosity allows to attain a nanoemulsion, the fluidity of which makes it comparable to a liquid system that may be atomized as a spray, increasing the indications and uses of the nanoemulsion.

However, it is also possible to formulate stable nanoemulsions characterised by an acidic pH within the range from 3 to 5, at which, though, an increase in viscosity may be observed, due to the arrangement of the ASP "coagel" in the form of liquid crystals, as in such a pH range the acidic ASP component may be insufficiently salificated. Thus, while the introduction of a base at least into the aqueous phase used for the manufacture of the nanoemulsion is a preferred aspect, its concentration does not need to be such as to give the nanoemulsion a basic or slightly acidic pH.

Advantageously, the alteration in transparency and viscosity of the nanoemulsion according to the invention is a phenomenon that is repeatedly reversible by changing the pH and concomitantly the ionization of ASP.

In a further embodiment, the nanoemulsion may comprise chitosan preferably introduced as an acidic solution (pH<4.5). Under acidic pH conditions, chitosan behaves as a polycation and, when an acidic chitosan solution is added to the nanoemulsion, formation of ionic bonds is noted between chitosan and the ascorbyl palmitate anionic molecules within the surface of the dispersed oil micelles. The establishment of such bonds then results in the formation of a coating by electrodeposition, the presence of which advantageously makes the nanoemulsion gastro-resistant.

The present invention also relates to a method for the manufacture of a nanoemulsion with a micelle size from 20 to 900 nm. The emulsification occurs by phase inversion exploiting the Phase Inversion Temperature (PIT) with the aid of a mechanical stirring device and by administering thermal energy to the system.

The first step of the method comprises setting up separately an aqueous phase comprising a base and a lipid phase comprising one or more polyoxyethylene sorbitan esters. The aqueous phase or the lipid phase, or both, further comprise ascorbyl palmitate. Preferably both the aqueous phase and the lipid phase comprise ascorbyl palmitate.

Subsequently, the two phases are heated at a temperature from 30 to 80° C., preferably from 40 to 70° C.

Then, the aqueous phase is poured out into the lipid phase under mechanical stirring, so as to obtain the nanoemulsion.

Finally, the so-obtained nanoemulsion is abruptly cooled down bringing the temperature of the nanoemulsion to room temperature (25° C.), for instance placing the nanoemulsion into a cold water bath.

Advantageously, the inventors of the present invention found out that using a combination of ascorbyl palmitate and one or more polyoxyethylene sorbitan esters allows for the manufacture of a nanoemulsion even at low temperatures, and anyway below 80° C., simply by mechanical stirring incorporating the aqueous phase into the oily phase. In this way, it is possible to reduce the consumption of energy in terms of thermal and mechanical energy to be provided in order to obtain emulsification. Furthermore, thanks to the possibility of operating at low temperatures (30-40° C.), the method according to the invention also allows for the emulsification of thermolabile or oxidation- and destabilization-sensitive active principles such as, for example, liposoluble vitamins, melatonin, coenzyme Q10 and its derivatives, flavonoids, and thermolabile drugs in general.

In one embodiment of the method according to the invention, one or more active principles may be added to the aqueous and/or lipid phases during their preparation. In another embodiment, the method may comprise the further step of (d) dispersing one or more active principles into the nanoemulsion by mechanical stirring.

The invention will now be further described by way of examples, the contents of which are not to be intended as limiting the scope of the present invention.

Example 1

A nanoemulsion was prepared with the components indicated in Table 1, wherein the amounts of the single components are expressed as w/w percentage per 100 grams of nanoemulsion, unless differently indicated. The lipid phase was prepared by vigorously stirring a medium-chain triglyceride (Delios V), ascorbyl palmitate, polysorbate 60, and glycerine, until a homogenous mixture was obtained. The aqueous phase was prepared by melting fructose and the preserving agents in water under stirring, adding ascorbyl palmitate and thereafter the NaOH solution, until a pH value of 7 and a progressive clearness of the phase were reached.

TABLE 1

| Phase | Component | Quantity |
| --- | --- | --- |
| Lipidic | Delios V | 4.00 |
|  | Polysorbate 60 | 4.00 |
|  | Ascorbyl palmitate | 0.55 |
|  | Glycerine | 5.00 |
| Aqueous | Ascorbyl palmitate | 0.30 |
|  | 30% NaOH in water | q.s. up to pH 7 |
|  | Potassium sorbate | 0.15 |
|  | Sodium benzoate | 0.15 |
|  | Fructose | 10.00 |
|  | Water | q.s. up to 100 |

Subsequently, the two phases were heated up to 50° C., to then start the emulsification under mechanical stirring (mechanical stirrer provided with a helical rotating rod, 10000 rpm), pouring out small sequential volumes of the lipid phase into the aqueous phase. The so-obtained nanoemulsion was cooled down to 25° C. and the pH adjusted between 4 and <4.5 with an 80% lactic acid solution or with citric acid.

The so-prepared nanoemulsion is stable, translucent, pale yellow, and has a pH between 4.0 and 4.5. The dimensional analysis of the particles was carried out by Dynamic Back Scattering, showing a micelle diameter within the range from 30 to 50 nm, both at time 0 from the emulsification and two weeks after the manufacture of the nanoemulsion.

Example 2

A nanoemulsion was prepared with the components indicated in Table 2, wherein the amounts of the single components are expressed as w/w percentage per 100 grams of nanoemulsion, unless differently indicated. The lipid phase was prepared by vigorously stirring a medium-chain triglyceride (Delios V), ascorbyl palmitate, polysorbate 60, and glycerine, until a homogenous mixture was obtained. The aqueous phase was prepared by melting fructose and the preserving agents in water under stirring, adding ascorbyl palmitate and thereafter the NaOH solution, until a pH value of 7 and a progressive clearness of the phase were reached.

TABLE 2

| Phase | Component | Quantity |
| --- | --- | --- |
| Lipidic | Delios V | 4.00 |
|  | Polysorbate 60 | 4.00 |
|  | Ascorbyl palmitate | 0.55 |
|  | Glycerine | 5.00 |
| Aqueous | Ascorbyl palmitate | 0.30 |
|  | 30% NaOH in water | q.s. up to pH 7 |
|  | Potassium sorbate | 0.15 |
|  | Sodium benzoate | 0.15 |
|  | Fructose | 10.00 |
|  | Water | q.s. up to 100 |
| Active principle | Melatonin | 0.50 |

Subsequently, the two phases were heated up to 50° C., to then start the emulsification under mechanical stirring (mechanical stirrer provided with a helical rotating rod, 10000 rpm), pouring out small sequential volumes of the lipid phase into the aqueous phase. The so-obtained nanoemulsion was cooled down to 25° C. and the melatonin was dispersed by vigorous stirring. Once a homogeneous dispersion of the melatonin was induced, obtaining a translucent system devoid of suspended or sedimented clusters, the pH was adjusted between 4 and <4.5 with an 80% lactic acid solution or with citric acid.

The so-prepared nanoemulsion is stable, translucent, pale yellow, and has a pH between 4.0 and 4.5. The dimensional analysis of the particles was carried out by Dynamic Back Scattering, showing a micelle diameter within the range from 30 to 50 nm, both at time 0 from the emulsification and two weeks after the manufacture of the nanoemulsion.

It was thus showed that the nanoemulsion according to the invention fully performs the appointed duty, since the combination of ascorbyl palmitate and one or more polyoxyethylene sorbitan esters allows to obtain a stable nanoemulsion having a reduced micelle diameter. Moreover, the nanoemulsion according to the invention proved to be able to carry pharmaceutical, cosmetic or foodstuff active principles, including thermolabile or oxidation-sensitive active principles. It was also found that the method according to the invention allows to provide a stable nanoemulsion having a reduced micelle diameter, with a reduced consumption of energy in terms of thermal and mechanical energy, due to the combination of ascorbyl palmitate and one or more polyoxyethylene sorbitan esters. The so-designed nanoemulsion, composition, and method are susceptible of numerous modifications and variations, all falling within the scope of the inventive concept; furthermore, all details may be substituted with other technically equivalent elements.

The invention claimed is:

1. A pharmaceutical formulation for the administration of melatonin in the form of a nanoemulsion, said nanoemulsion consisting of an aqueous phase and a lipid phase, said aqueous phase comprising a base, said lipid phase comprising a polyoxyethylene sorbitan ester, the said aqueous phase or lipid phase, or both, further comprising ascorbyl palmitate, wherein said nanoemulsion comprises melatonin as an active agent in an amount from 0.1% to 10% w/t, wherein in the nanoemulsion the emulsifying components consist of polyoxyethylene sorbitan ester and ascorbyl palmitate as the only emulsifying components, wherein in the nanoemulsion ascorbyl palmitate is present in an amount from 0.3 to 2% by weight and said polyoxyethylene sorbitan ester is present in an amount from 0.2 to 10% by weight and wherein said nanoemulsion comprises micelle sizes from 20 to 900 nm.

2. The pharmaceutical formulation of claim 1, wherein both the aqueous phase and the lipid phase comprise ascorbyl palmitate.

3. The pharmaceutical formulation of claim 1, wherein the polyoxyethylene sorbitan ester is selected from the group consisting of: polysorbate 20, polysorbate 40, polysorbate 60, polysorbate 65, polysorbate 80 and any combination thereof.

4. The pharmaceutical formulation of claim 1, wherein the micelle size is from 20 to 200 nm.

5. The pharmaceutical formulation of claim 1, wherein the base is selected from the group consisting of: L-arginine, L-lysine, a peptide, aminomethylpropanol, an alkaline metal hydrate, an alkaline earth metal hydrate, and any combination thereof.

6. The pharmaceutical formulation of claim 1, wherein the aqueous phase further comprises one or more preserving agents selected from the group consisting of: potassium sorbate, sodium benzoate, parabens, and any combination thereof.

7. The pharmaceutical formulation of claim 1, wherein the lipid phase comprises one or more lipids selected from the group consisting of: coconut oil, wheat germ oil, sunflower oil, olive oil, a medium-chain triglyceride, and any combination thereof.

8. The pharmaceutical formulation of claim 7, wherein the one or more lipids are present in an amount from 0.1 to 10% w/w.

9. The pharmaceutical formulation of claim 1, further comprising one or more polyols in an amount from 0.1 to 40% w/w.

10. The pharmaceutical formulation of claim 9, wherein the one or more polyols are selected from the group consisting of: glycerine, propylene glycol, sorbitol, mannitol, fructose, sucrose, glucose, trehalose, and honey.

11. The pharmaceutical formulation of claim 1, further comprising active agents selected from the group consisting of: flavonoids, flavones, flavanones, isoflavones, essential oils, terpenes, plant saponins, liposoluble vitamins, vitamin cofactors, enzyme cofactors, amino acids, oligopeptides, peptides, saturated fatty acids, unsaturated fatty acids, and any combination thereof.

12. The pharmaceutical formulation of claim 1, having a pH from 3 to 7.

13. The pharmaceutical formulation of claim 1, further comprising an acidic pH chitosan solution.

14. A method for making the pharmaceutical formulation of claim 1, comprising the following sequential steps:
(a) preparing an aqueous phase comprising a base and a lipid phase comprising a lipid and a polyoxyethylene sorbitan ester, wherein the aqueous phase or the lipid phase, or both, further comprise ascorbyl palmitate;
(b) heating the aqueous and lipid phases at a temperature from 30 to 80° C.;
(c) pouring out the aqueous phase into the lipid phase under mechanical stirring, so as to obtain the nanoemulsion;
(d) bringing the nanoemulsion to room temperature, and
(e) dispersing melatonin as an active agent into the nanoemulsion by mechanical stirring,
wherein polyoxyethylene sorbitan ester and ascorbyl palmitate are included as the only emulsifying components.

* * * * *